(12) United States Patent
Crouzet et al.

(10) Patent No.: US 6,214,592 B1
(45) Date of Patent: Apr. 10, 2001

(54) ENZYMES AND MICROORGANISMS HAVING AMIDASE ACTIVITY FOR HYDROLYSING POLYAMIDES

(75) Inventors: Joël Crouzet, Sceaux; Olivier Favre-Bulle; Catherine Jourdat, both of Lyons; Anne-Marie Le Coq, Issy les Moulineaux; Dominique Petre, Lyons, all of (FR)

(73) Assignee: Rhone-Poulenc Fibres et Polymeres S.A., Courbevoie Cedex (FR)

( * ) Notice: Subject to any disclaimer, the term of this patent is extended or adjusted under 35 U.S.C. 154(b) by 0 days.

(21) Appl. No.: 09/000,064

(22) PCT Filed: Jul. 17, 1996

(86) PCT No.: PCT/FR96/01119

§ 371 Date: Apr. 3, 1998

§ 102(e) Date: Apr. 3, 1998

(87) PCT Pub. No.: WO97/04084

PCT Pub. Date: Feb. 6, 1997

(30) Foreign Application Priority Data

Jul. 18, 1995 (FR) ...................................... 9508916

(51) Int. Cl.[7] .............................. C12P 13/02; C12N 9/78; C12N 9/80
(52) U.S. Cl. ......................... 435/129; 435/227; 435/228
(58) Field of Search ................... 435/227, 228, 435/129

(56) References Cited

PUBLICATIONS

Amino Acid Nucleic Acid, vol. 33, 1976, pp. 129–139, XP000605985, Fukumura et al, "Microbial Conversion of Some Synthetic Cyclic Amides".
Database WPI, Week 6800, Derwent Publications Ltd., London, GB, XP002015967 & JP 44 017 992 (Toyo Rayon KK) (no date given).
J. Bacteriol., vol. 174, No. 24, (1992), pp. 7948–7953, Negoro et al, "A New Nylon Oligomer Degradation Gene (nylC) on Plasmid pOAD2 from Flavobacterium sp".
Biodegradation, vol. 5, No. 3–4, Dec. 1994, pp. 185–194, Negoro et al, "The Nylon Oligomer Biodegradation System of Flavobacterium and Pseudomonas".
Nature, vol. 301, Nov. 10, 1983, pp. 203–206, Okada et al, "Evolutionary Adaptation of Plasmid–Encoded Enzymes for Degrading Nylon Oligomers".
Negoro, S., et al. (1984) J. Biol. Chem. 259 (22), 13648–13651.*
Kinoshita, S., et al. (1981) Eur. J. Biochem. 116, 547–551.*
Tsuchiya, K. et al. (1989) J. Bacteriol. 171, 3187–3191.*

* cited by examiner

Primary Examiner—Charles L. Patterson, Jr.
(74) Attorney, Agent, or Firm—Burns, Doane, Swecker & Mathis, L.L.P.

(57) ABSTRACT

The present invention relates to an enzyme with amidase activity, particularly towards substrates of the oligomer type derived from PA 6.6 (formula I) and/or PA 6 (formula II), said enzyme being characterized by a ratio $$Ra = \frac{\text{enzymatic activity towards (poly)amide substrates of formula (I)}}{\text{enzymatic activity towards (poly)amide substrates of formula (II)}} = \frac{E.A.(I)}{E.A.(II)}$$

which is greater than 2, preferably greater than or equal to 10 and particularly preferably greater than or equal to 50.

More precisely, this enzyme consists of the peptide sequence corresponding to the attached sequence SEQ ID NO: 2.

The invention further relates to the DNA which codes for this polypeptide SEQ ID NO: 2 and whose sequence corresponds to the attached sequence SEQ ID NO: 1.

The invention further relates to the microorganisms capable of producing this enzyme and to the hydrolysis process in which this enzyme and/or these microorganisms are applied.

17 Claims, 2 Drawing Sheets

ENZYMES AND MICROORGANISMS HAVING AMIDASE ACTIVITY FOR HYDROLYSING POLYAMIDES

TECHNICAL FIELD

The present invention relates in general terms to the enzymatic hydrolysis of amides, especially secondary amides.

The invention relates more precisely to enzymes and/or microorganisms which are capable of being used in the enzymatic hydrolysis of amide groups, preferably on substrates containing at least one amide group, for example polyamides (PA). The invention further relates to the genetic material in their production and to the microorganisms which contain this genetic material and exhibit this amidase activity.

PRIOR ART

In this field, SMITH R. et al. are the authors of an article published in "Journal of Biomedical Materials Research (1987), vol. 21, p. 991–1003" and disclose the bringing of samples of polyamide 66 labeled with carbon 14 into contact with enzymes of the papain, trypsin and α-chymotrypsin type. These known polypeptides degrade polyamide 66 slightly, but the hydrolysis is not sufficiently significant to be able to be exploited on the industrial scale.

It is also known, through the article by KINOSHITA et al. (Eur. J. Biochem. 116, 547–551, 1981), that Flavobacterium sp KI 72 is able to produce a first enzyme ($E_1$) which catalyzes the hydrolysis of cyclic dimers of 6-aminohexanoic acid to linear dimers of this same acid, and a second enzyme ($E_2$) which is capable of converting this linear dimer to two molecules of 6-aminohexanoic acid or aminocaproic acid. The enzymatic pathway in question is summarized below.

The activity of the linear amidase $E_2$ is optimal for the dimers and decreases as the degree of polymerization increases, no longer being significant beyond oligomers with a degree of polymerization ($DP_n$) of 7.

In their article published in "Journal of Bacteriology, June 1989, p. 3187–3191, vol. 171 no. 6", TSUCHIYA et al. teach that a high degree of homology exists between the enzymes $E_1$ from Flavobacterium sp KI 72 and one of the enzymes derived from Pseudomonas sp NK 87. These enzymes $E_1$ and homologs, and the enzymes $E_2$, more particularly the latter, are said to be active on oligomers or polyamides (PA 6) of the formula where: $2 \leq n \leq 20$.

The disadvantage of these enzymes derived from Flavobacterium or Pseudomonas is that they have relatively low specific activities towards oligomers, said activities amounting to at most only 1.05 micromol of amninocaproic acid produced per minute and per milligram of protein from a substrate consisting of a trimer. Furthermore, these enzymes are specific for homo-oligomers and are found to have a poor activity towards co-oligomers.

Moreover, the strain Flavobacterium sp KI 72 was at the center of the discovery of another gene, called nyl-c, coding for a polyamidase $E_3$ active towards substrates of the PA 6 type.

The following is one of the literature references referring to $E_3$ produced under the control of nyl-c: "NEGORO et al. (1992)—Journal of Bacteriology, vol. 174, p. 7948–7953".

It appears that $E_3$ has a relatively low specificity for oligomers of nylon PA 66 compared with oligomers of nylon PA 6. The resulting ratio $$Ra = \frac{\text{enzymatic activity towards PA 66}}{\text{enzymatic activity towards PA 6}}$$

is of the order of 2, the activities being expressed as the amount of substrate hydrolyzed per unit time and per unit amount of hydrolyzing substance used. Examples of the substrates in question are tetramers and trimers of PA 66 and PA 6.

It is thus apparent that the prior art does not comprise means for the enzymatic hydrolysis of amide groups which have a high performance, are viable and can be applied to amides, including especially secondary amides, of a variety of types, particularly of the co-oligomer type.

DISCLOSURE OF THE INVENTION

One of the essential objects of the present invention is thus to propose novel enzymes with amidase activity, genetic material for producing them, and microorganisms containing this genetic material, said enzymes and microorganisms being simultaneously characterized by satisfactory yields in the hydrolysis of amides from substrates of the co-oligomer and homo-oligomer type and by a pronounced specificity towards co-oligomers (e.g. PA 66). Such an activity is capable of providing access to an industrially valuable method of regenerating monomers, especially of PA 66 (recycling).

Therefore, after lengthy and laborious research, the Applicant succeeded in isolating and characterizing a novel enzyme of the amidase type formed by one or more polypeptides which, in particular, can be derived from novel microorganisms isolated from the biotype and/or novel recombinant microorganisms obtained from these natural microorganisms.

This enzyme is used either as such or, preferably, in the form of recombinant microorganisms which generate them.

The present invention consequently relates to an enzyme with amidase activity, particularly towards substrates of the polyamide type having at least one of the following formulae:

(I)

in which:

A and B are monomer units, $R^1$ and $R^3$ are identical or different—preferably different—divalent radicals representing a substituted or unsubstituted, linear or branched (cyclo)alkylene, an arylene or an arylalkylene, the aromatic radicals optionally being polycondensates and the number of carbons in the alkylenes being greater than or equal to 4, preferably between 4 and 12, $R^2$ corresponds to identical or different—preferably identical—radicals selected from hydrogen and/or alkyl radicals advantageously having from 1 to 6 carbons,

X is:
either $X^1$=OH, OM or $OR^4$, where M is selected from metals, preferably alkali metals and alkaline earth metals, and $R^4$ is a linear or branched alkyl containing from 1 to 6 carbon atoms, or $X^2$= where $R^2$ and $R^3$ are as defined above and $R^5$ and $R^6$, which are identical or different, have the same definition as that given above for $R^2$, Y is:
either $Y^1$=hydrogen,
or $Y^2$= where $R^1$ is as defined above and Z is hydrogen, $M^1$ defined in the same way as M, or $R^4$, with the following conditions:
a—if X=$X^1$, then Y=$Y^1$,
b—if X=$X^2$, then Y=$Y^2$ or $Y^1$,
and, finally, p is between 1.5 and 10, preferably between 1.5 and 5;
or (II)

in which:
$R^2$ and $R^3$ are as defined above,
U and V respectively have the same definitions as those given above for $X^1$ and $Y^1$ in formula (I),
and q=1 to 20.

One very advantageous feature of the enzyme according to the invention is the fact that its specific enzymatic activity ($U_s$) is much greater towards the co-oligomers of formula (I) than towards the homo-oligomers of formula (II).

Thus the enzyme according to the invention—also called PAM I—is characterized by a ratio $$Ra = \frac{\text{Enzymatic Activity towards (poly)amide substrates of formula (I)}}{\text{Enzymatic Activity towards (poly)amide substrates of formula (II)}}$$

which is:

greater than 2;

preferably greater than or equal to 10;

and particularly preferably greater than or equal to 50.

In the ratio Ra, the enzymatic activity is expressed in mol of hydrolyzed substrate x $h^{-1} \times g^{-1}$ of enzyme or dry cells producing the enzyme used.

The conditions of measurement of these activities are given below:

reaction medium=100 mM phosphate buffer, volume=400 µl, temperature=30° C., pH=7, concentration of dry cells=2.5 g/l.

The enzyme according to the invention is also characterized by its primary structure, which is given by the attached amino acid sequence SEQ ID NO: 2.

This also embraces any polypeptide having a degree of homology of at least 50% with this sequence SEQ ID NO: 2.

The primary or even quaternary structure of the enzyme according to the invention constitutes one of its numerous novel characteristics.

In addition to this structural characterization, however, it is possible to envisage the enzyme according to the invention through its activity towards some of its specific substrates.

As described above, the latter are polyamides and, more precisely, oligomers whose repeat units have formulae (I) and/or (II) mentioned above. The repeat units (I) are advantageously formed of two monomer units, A and B, which are respectively dicarbonyl and diamine units and are joined together by a secondary amine group.

In one preferred modality of the invention:
the monomer A is a residue where r is between 4 and 12 and is preferably equal to 4, and the monomer B is a residue where s is between 4 and 12 and is preferably equal to 6.

Thus, for the substrates (I), a preferred example of a dimer is that formed by

A — Adipic acid
B — Hexamethylene diamine

The corresponding polyamide is PA 6.6.

The repeat units (II), on the other hand, are preferably formed by monomer units denoted as in which c is a skeleton of the amino acid type whose end groups (a) and (b) are carboxyl and amino groups respectively.

A typical example of is a derivative of ε-aminocaproic acid, the monomer of polyamide 6 (PA 6).

The following may be mentioned among the oligomers of the polyamide type which are suitable for the invention:

the polyamide oligomers obtained by the polycondensation of saturated aliphatic carboxylic diacids having from 6 to 12 carbon atoms with saturated aliphatic primary diamines having from 6 to 12 carbon atoms, the polyamino acid oligomers obtained either by the direct homopolycondensation of an ω-aminoalkanoic acid containing a hydrocarbon chain having from 4 to 12 carbon atoms, or by the hydrolytic opening and polymerization of the lactams derived from these acids, the copolyamide oligomers obtained from the starting monomers of the above-mentioned polyamides, it also being possible for the acid component of these copolyamides to consist partly of an aromatic acid such as terephthalic acid and/or isophthalic acid, and mixtures of these polyamide oligomers.

The following may be mentioned as illustrative examples of the polyamides obtained by the polycondensation of diacids and diamines:

polyamide 4,6 (polymer of tetramethylenediamine and adipic acid),
polyamide 6,6 (polymer of hexamethylenediamine and adipic acid) (PA 6.6),
polyamide 6,9 (polymer of hexamethylenediamine and azelaic acid),
polyamide 6,10 (polymer of hexamethylenediamine and sebacic acid),
polyamide 6,12 (polymer of hexamethylenediamine and dodecanedioic acid).

The following may be mentioned as illustrations of suitable polyamino acids:
polyamide 4 (polymer of 4-aminobutanoic acid or γ-butyrolactam),
polyamide 5 (polymer of 5-aminopentanoic acid or δ-amylolactam),
polyamide 6 (polymer of ε-caprolactam),
polyamide 7 (polymer of 7-aminoheptanoic acid),
polyamide 8 (polymer of capryllactam),
polyamide 9 (polymer of 9-aminononanoic acid),
polyamide 10 (polymer of 10-aminodecanoic acid),
polyamide 11 (polymer of 11-aminoundecanoic acid),
polyamide 12 (polymer of 12-aminododecanoic acid or laurolactam).

The following may be mentioned as illustrative examples of copolyamides:
polyamide 6,6/6,10 (copolymer of hexamethylenediamine, adipic acid and sebacic acid),
polyamide 6,6/6 (copolymer of hexamethylenediamine, adipic acid and caprolactam).

Without implying a limitation, the preferred substrates according to the invention are polyamide oligomers obtained by the polycondensation of diacids A and diamines B. particularly oligomers of PA 6.6.

The number of monomers A and B, on the one hand, or on the other, in the substrates (I) and (II) according to the invention is advantageously between 3 and 8, preferably between 2 and 6. It should be pointed out that this number of monomer residues in the oligomer or polymer molecules will also be called $DP_n$ in the remainder of the present disclosure.

Characteristic substrates (I) are e.g. advantageously water-soluble oligomers such as BAB and ABAB, excluding the trimers ABA.

These particular substrates are among the substrates (I) and (II) which can be hydrolyzed, with a very high performance, by the enzyme of the invention and/or its biological precursors.

When the enzymatic substrates are oligomers containing monomers A and B, the final hydrolysis products can be dimers AB and monomers B.

When the substrates are oligomers (B) (II)

the final hydrolysis products can be monomers

The enzyme according to the invention can also be characterized through its activity and/or its affinity towards some of the above-mentioned substrates (I) and (II).

Thus, according to a first advantageous characteristic, the amidase in question is:

firstly active towards a substrate (I) formed by a tetramer of the type ABAB, and secondly capable of converting this substrate to two dimers AB with a specific enzymatic activity ($U_s$)—expressed in μmol of AB produced x $h^{-1}$ x $mg^{-1}$ of protein and measured under given conditions—which is greater than 60, preferably greater than or equal to 100 and particularly preferably greater than or equal to 1000.

A second advantageous characteristic of this amidase is that it is:

active towards a substrate (I) formed by a trimer BAB, and capable of converting this trimer to a dimer AB and a monomer B with a specific enzymatic activity ($U_s$)—expressed in μmol of AB produced/h.mg of enzyme and measured under given conditions—which is greater than 100 and preferably greater than or equal to 500.

A third advantageous characteristic of this amidase is that it is:

active towards substrates (I) formed by oligomers whose $DP_n$ is between 3 and 20, preferably between 3 and 10, and capable of converting these oligomers to a monomer B, a dimer AB and a trimer ABA.

The enzymatic activity of the pure amidase is measured under the following conditions:

phosphate buffer temperature=30° C.

substrate concentration=1.4 g/l pH=7.5.

As already indicated above, the use of the enzyme of the invention in the enzymatic hydrolysis of amides can consist in using either only the enzyme per se, or only biological precursors (wild-type or recombinant microorganisms) which produce said enzyme, or a mixture of both.

As far as its origin is concerned, the enzyme according to the invention was isolated in particular from a natural microorganism of the genus Corynebacterium.

From that starting point, it was also to the Applicant's credit to have identified the gene under whose control the amidase according to the invention is synthesized, it being precisely this technical advance which enables recombinant microorganisms to be used.

Consequently, a further subject of the invention is a DNA sequence coding for an enzyme with amidase activity, particularly towards substrates (I) and (II) as defined above, characterized in that it is selected from the following sequences:

the DNA sequence corresponding to the attached sequence SEQ ID NO: 1 and coding for an enzyme with amidase activity, an analog of this sequence which results from the degeneracy of the genetic code, and a DNA sequence which:

hybridizes with one of these sequences or with a fragment thereof, possesses an identity of more than 50% with one of these sequences or with a fragment thereof, and codes for an enzyme with amidase activity.

The enzymes resulting from the (hyper)expression of a DNA sequence of the type defined above are naturally included in the field of the invention.

The (hyper)expression can be obtained within recombinant microorganisms (e.g. those including one or more plasmids) by selecting an appropriate expression cassette comprising one or more promoters and one or more ribosome binding sites which induce (hyper)expression.

On the subject of recombination, one of the preferred recombinant microorganisms according to the invention is the one consisting of the E. coli strain which contains plasmid pXL2564, a derivative of the strain referenced and deposited in the Collection Nationale de Cultures de Microorganismes under no. I 1495 on Nov. 29, 1994.

Figure 2:
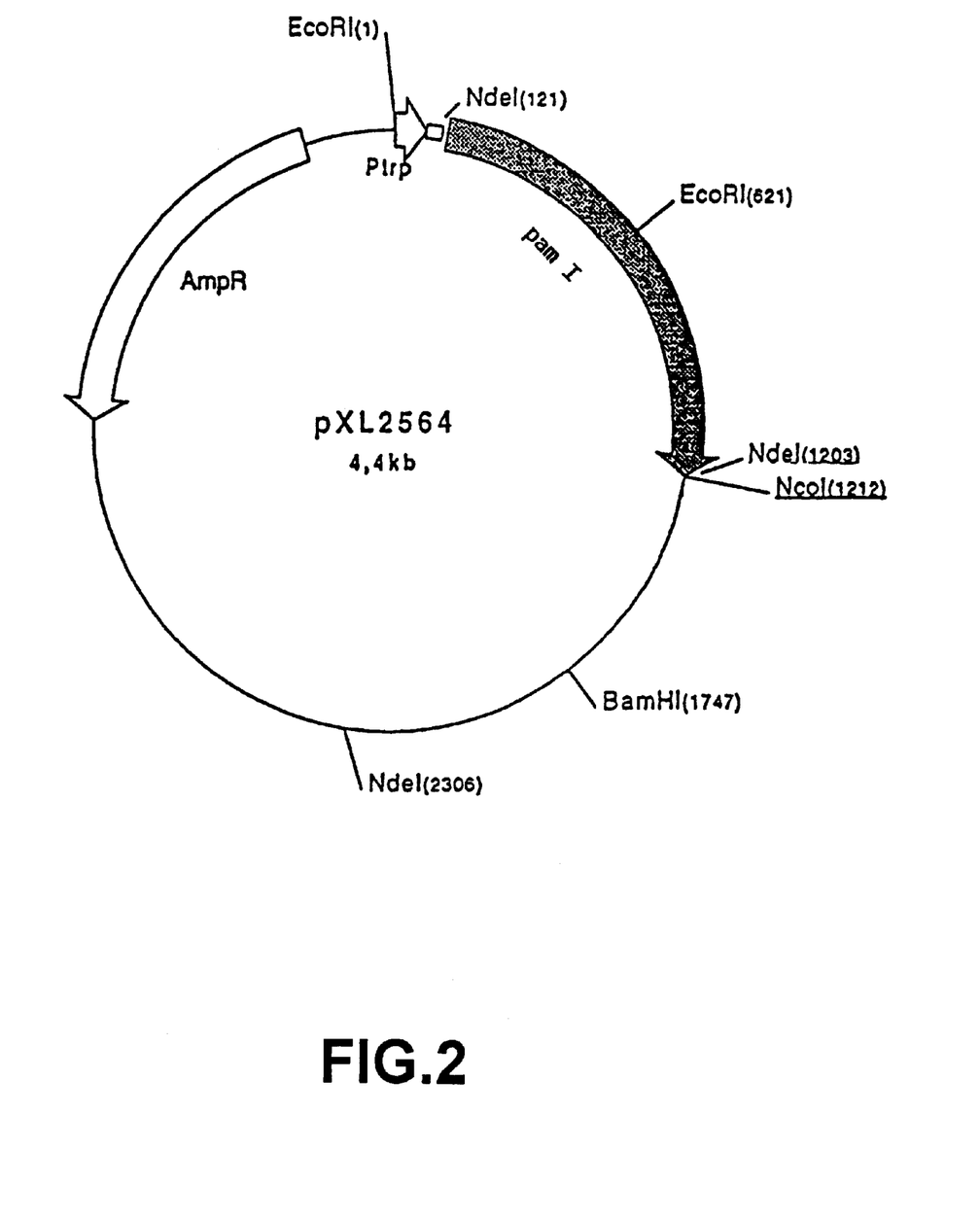
FIG. 2 shows the restriction map of plasmid pXL2564 containing the pam I gene coding for the amidase according to the invention, a gene conferring ampicillin resistance and the Ptrp-RBScII expression cassette controlling the amidase gene.

This E. coli strain contains plasmid pXL2564, said plasmid carrying SEQ ID NO: 1 and an expression cassette which can be for example the one shown in FIG. 2 attached: Ptrp-RBSCII.

In more general terms, the present invention relates to all the novel recombinant or non-recombinant microorganisms which are capable of producing the atidase according to the invention and advantageously possess the genetic information contained in the above-defined sequence or sequences forming subjects of the invention.

It is self-evident that the amidases produced by these microorganisms are wholly covered by the present invention.

The particular characteristics of these microorganisms are a capacity to hydrolyze the amide groups of a polyamide compound comprising at least one amide group. and, more precisely, a specific selectivity and hydrolytic activity towards the substrates (I) and (II) defined above and, even more particularly, towards the substrates (I) relative to the substrates (II).

In the case of the substrates (I), these oligomers are for example the water-soluble oligomers mentioned above: ABAB and/or BAB, inter alia.

Advantageously, the microorganisms according to the invention are capable of hydrolyzing at least one substrate formed by a polyamide oligomer and, more particularly, by a tetramer ABAB and/or a trimer BAB, which are destined to be converted to monomers B and dimers AB, the microorganisms being capable of performing the hydrolysis with an activity which is:

expressed in g of hydrolyzed substrate/h.g of dry cells and measured under given conditions, and greater than or equal to 50, preferably 80 and particularly preferably 100.

This activity is measured at a temperature of the order of 30° C., at a pH of 7 in a phosphate buffer (100 mM), with magnetic stirring, in a volume of reaction medium of 400 µl and at a substrate concentration of 2.5 g/l.

To optimize the performance characteristics of these microorganisms, they are advantageously equipped, according to the invention, with:

at least one protein agent for assisting the folding of the polypeptides which they synthesize, and particularly the enzymes as defined above, and/or genes coding for such an agent.

This agent is present in an amount greater than that corresponding to the base level of the microorganism in question.

The agent is preferably the GroE chaperone of E. Coli or its homolog of eukaryotic or prokaryotic origin.

The present invention further relates to a process for the hydrolysis of substrates which are at least partly formed by the substrates (I) and/or (II) as defined above, characterized in that it consists in using at least one enzyme and/or at least one of the microorganisms as presented above.

It may be advantageous, according to the invention, to have several enzymes with complementary spectra. Therefore, one of the variants of the above-mentioned process can be to have the use of at least one other type of enzyme and/or at least one of its wild-type and/or recombinant and/or analogous biological precursors. In this variant, the substrates consist at least partly of oligomers whose DP, is less than 40, preferably 20 and particularly preferably 12, and which are derived from polyamides at least originating from polycondensation between diacid monomers (A) and diamine monomers (B).

The hydrolysis process according to this variant is characterized in that:

it produces oligomers with a degree of polymerization ($DP_n$) less than or equal to 8, preferably 4, and particularly preferably produces monomers A and B, and the following are used:

at least one enzyme and/or at least one microorganism as defined above, and at least one other type of enzyme and/or to at least one of its wild-type and/or recombinant biological precursors, said enzyme preferably being an enzyme $E_2$ produced under the control of the nyl-B gene of Flavobacterium sp KI 72.

The complementary enzyme $E_2$ produced by nyl-B is described in KINOSHITA et al. (Eur. J. Biochem. 116, 547–551, 1981) or in TSUCHIYA et al. ("Journal of Bacteriology, June 1989, p. 3187–3191, vol. 171 no. 6").

In the absence of enzyme $E_2$, the process would preferentially lead in practice to oligomers of $DP_n \leq 4$ and very particularly to dimers AB.

Oligomers hydrolyzable by the above enzymes can be obtained by thermal and/or chemical (acid) lysis of the groups of the amide type, especially by the lysis of polymers or oligomers of high $DP_n$.

Other advantageous modalities of the process according to the invention use especially biological precursors of the enzyme (or enzymes) and a culture medium comprising, for example:

a carbon source preferably comprising at least one compound containing at least one amide group, said carbon source optionally comprising a complement advantageously selected from carbohydrates, sucrose being particularly preferred, and optionally a compound capable of inducing enzyme production without being( consumed by the biological precursors, said compound preferably being selected from amides.

The process according to the invention for the enzymatic hydrolysis of amides can have numerous applications, for example in organic synthesis for the manufacture of compounds from amide compounds or for the treatment of materials containing polyamide.

In particular, it could be of value within the framework of regenerating the starting materials of polyamide polymers.

The Examples which follow provide an illustration of the characteristics, variants and advantages of the present invention without however limiting its scope.

DESCRIPTION OF THE ATTACHED FIGURES

The sequence listing, established according to WIPO standard ST 23, comprises the following sequences.

SEQ ID NO: 1 DNA coding for the amidase according to the invention.

SEQ ID NO: 2: polypeptide forming the amidase according to the invention.

The meanings of the abbreviations used in the remainder of the description are given below:

SSC: buffer commonly used for hybridizations, containing sodium citrate and NaCl (20×SSC=NaCl 3M–sodium citrate pH 7, 0.3 M),
SDS: sodium dodecylsulfate,
SDS-PAGE: electrophoresis gel based on sodium dodecylsulfate and polyacrylamide,
IPTG: isopropyl-β-D-thiogalactopyranoside,
HPLC: high performance liquid chromatography.

EXAMPLES

The isolation of the original strains, the purification and peptide sequencing of the polyamide hydrolase according to the invention (PAM I=SEQ ID NO: 2), and the cloning of the pam I gene coding for PAM I, were carried out by the current conventional techniques.

Example I

Recombination: Expression of PAM I in *E. Coli*

Figure 1:
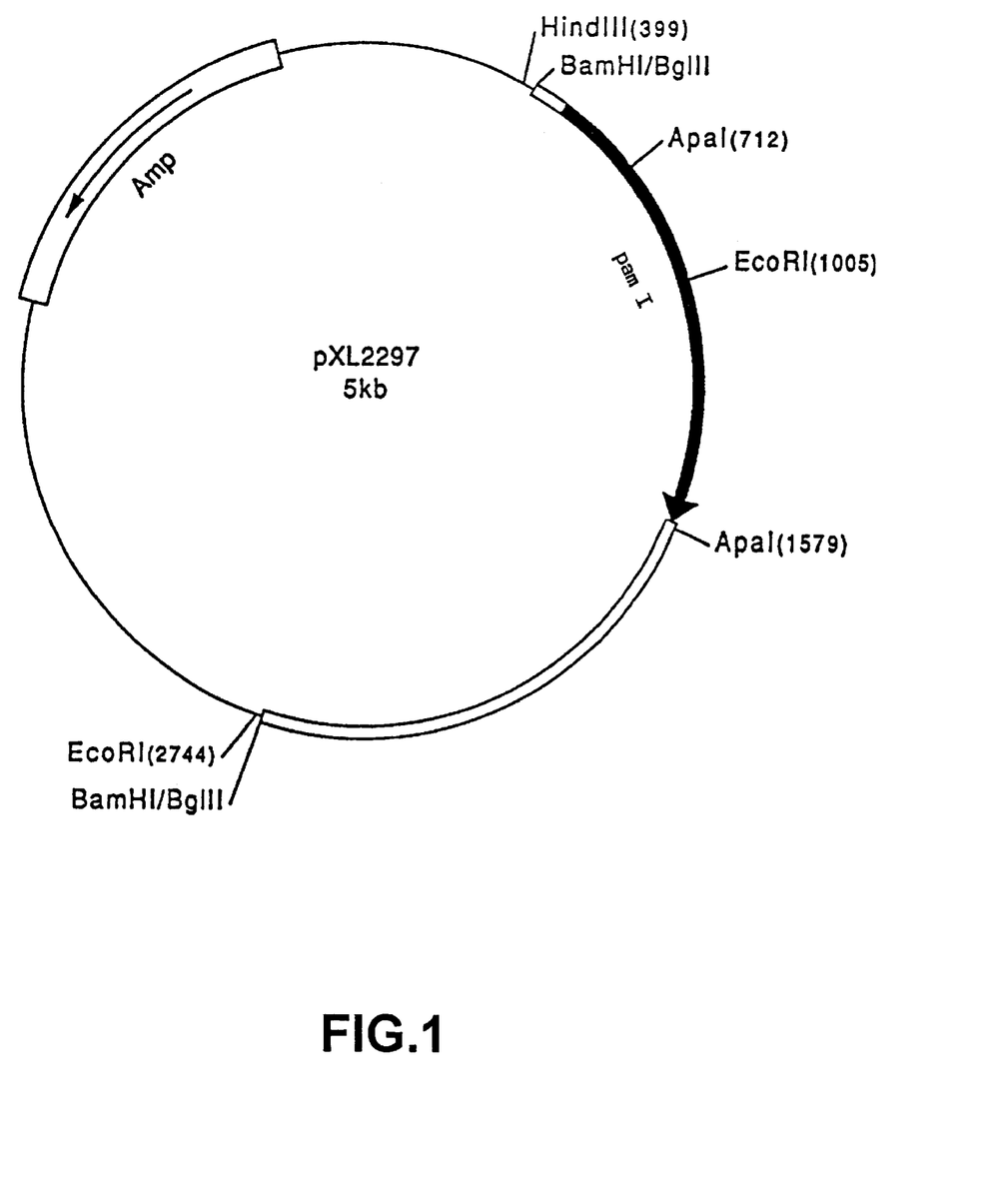
FIG. 1 shows the restriction map of plasmid pXL2297 containing the gene coding for the amidase according to the invention and accommodated by the strain deposited in the CNCM under no. I 1495 on Nov. 29, 1994.

A construction was produced in which the pam I gene (coding for the enzyme PAM I), preceded by the ribosome binding site of the phage λ CII gene, is expressed from the *E. coli* tryptophan operon promoter. To do this, an NdeI restriction site was created at the pam I initiation codon by the PCR technique using, as template, plasmid pXL2297 (FIG. 1) accommodated by the strain I 1495 deposited in the CNCM on Nov. 29, 1994. The 208 bp NdeI-ApaI fragment containing the 5' end of the pam I gene was amplified by PCR, care being taken to introduce a HindIII site upstream of the NdeI site by means of the pair of nucleotide primers (5'-AGCAAGCTTGGAGGCCATATGAATACGAC-3') and (5'-CACCGGTGGGCCCCTC-3'). The amplified HindIII-ApaI fragment was cloned into pUC29 (Benes et al. (1993), Gene 130: 151–152) digested by HindIII and ApaI, and the pam I gene was reconstituted by introducing the 867 bp ApaI fragment of pXL2297 at the ApaI site. An NcoI site is thus located about thirty nucleotides downstream of the pain I stop codon. The adjacent 500 bp NdeI-EcoRI and 600 bp EcoRI-NcoI fragments of this plasmid were inserted into pXL2158 (patent FR 92-09 882) digested at the NdeI site located immediately downstream of the tryptophan promoter.

Thus plasmid pXL2564 (described in FIG. 2) is a derivative of pBR322 (Sucliffe (1978), Nucleic Acid Res. 5: 2721) containing a gene conferring ampicillin resistance and the pam I gene under the control of the Ptrp-RBScII expression cassette.

Plasmid pXL2564 was introduced into the *E. coli* strain TG1, the microorganisms being selected on ampicillin LB. A clone containing pXL2564 (called strain PAM I) was transferred twice onto agar dishes and cultured at 37° C. in M9 glucose medium containing 100 μg/ml of ampicillin, according to the procedure described in patent FR 2 694 571.

The efficacy of the coexpression of the GroE chaperone to obtain a soluble form of polyamidase I was tested by introducing plasmid pXL2035 (patent FR 2 694 571) into the strain TG1 (pXL2564). The resulting strain was cultivated under the same conditions in the presence of 50 mg/l of kanamycin.

The results show that, with this novel recombinant strain, polyamidase I is produced essentially in soluble and cleaved form.

Example II

Comparison of the Amidase Activities of the Recombinant Strain Expressing $E_3$ and the Recombinant Strain Expressing PAM I, as Obtained in Example I II.1 Culture of the Strains:

The strain expressing PAM I was cultivated as indicated in Example I.

The strain expressing $E_3$ is obtained by introducing plasmid pUCL3 into the *E. coli* strain TGI described in the reference "NEGORO et al. (1992)—Journal of Bacteriology, vol. 174, p. 7948–7953". This strain was cultured at 37° C. in M9 medium supplemented with 100 mg/l of ampicillin and inoculated at 1% (v/v) with a pre-culture. An inducer (IPTG 1 mM) was added after 4 hours 30 minutes of incubation. The preculture is composed of 10 ml of the same M9 medium supplemented with 100 mg/l of ampicillin and inoculated with colonies originating from an agar dish. When culture is complete, the cell production is determined via a dry extract obtained by the drying, overnight at 105° C., of a cell residue obtained after centrifugation (10 min at 12,000 g). The M9 medium is composed of:

| | |
|---|---|
| glucose | 4 g/l |
| $KH_2PO_4$ | 3 g/l |
| $Na_2HPO_4$ | 7 g/l |
| $MgSO_4$ | 1 m/M |
| $NH_4Cl$ | 1 g/l |
| NaCl | 0.5 g/l |
| $CaCl_2$ | 1 mM |
| casamino acids | 4 g/l |
| thiamine HCl | 10 mg/l |

II.2 Activity of the Strains:

The cell residues, obtained as indicated above, are taken up with a 0.1 M Tris-HCl, 5 mM EDTA buffer, pH 8.0, containing 1% (v/v) of toluene, and incubated for 1 hour at 0° C. After centrifucation, the treated residues are resuspended in a 0.1 M phosphate buffer, pH 7.

The amidase activity of the cell suspensions of the strains expressing $E_3$ and PAM I was tested on the oligomers of $DP_n$ 2 to 6 for PA 6 and those of $DP_n$ 2 to 4 for PA 66.

The PA 6 oligomers of $DP_n$ 2 to 6 are called CAP 2 to CAP 6 respectively.

The results are listed in Table I below.

The activity is expressed in mmol of hydrolyzed substrate/hour/g of dry cells.

TABLE I

| Substrate | Reaction | Activity of the strain expressing PAM I | Activity of the strain expressing $E_3$ |
|---|---|---|---|
| ABAB | ABAB → AB + AB | 117 | 0.263 |
| BAB | BAB → AB + B | 131 | 0.067 |
| ABA | ABA → | 0 | 0 |
| AB | AB → | 0 | 0 |
| CAP 2 | CAP 2 → | 0 | 0 |
| CAP 3 | CAP 3 → CAP 2 + CAP 1 | 0.29 | 0.040 |
| CAP 4 | CAP 4 → CAP 2 + CAP 2 | 1.79 | 0.140 |
| CAP 5 | CAP 5 → CAP 3 + CAP 2 | 0.92 | 0.089 |
| CAP 6 | CAP 6 → CAP 3 + CAP 2 | 0.49 | 0.024 |

Operating conditions: [strain expressing $E_3$]=2.5 g/l of dry extract; [strain expressing PAM I]=2.5 g/l of dry extract for the nylon 6 oligomers and 0.125 g/l of dry extract for the nylon 66 oligomers; [oligomers] #2.5 g/l; 0.1 M phosphate buffer, pH=7; volume 400 µl; T=30° C.; magnetic stirring.

For the strain expressing $E_3$, the kinetics were measured over 3 hours for hydrolysis of the nylon 6 and 66 oligomers.

For the strain expressing PAM I, the kinetics were measured over 1 hour for hydrolysis of the nylon 6 oligomers and over 15 minutes for hydrolysis of the nylon 66 oligomers.

The hydrolytic activities of the strain expressing $E_3$ towards the nylon 6 and 66 substrates are of the same order of magnitude:

0.263 mmol of hydrolyzed ABAB/h/g of dry cells and 0.140 mmol of hydrolyzed CAP 4/h/g of dry cells (a factor of 2 between these activities).

PAM I is more specific for the nylon 66 oligomers than for the nylon 6 oligomers:

117 mmol of hydrolyzed ABAB/h/g of dry cells and 1.79 mmol of hydrolyzed CAP 4/h/g of dry cells (a factor of 65 between these activities).

This characteristic demonstrates the novelty of the enzyme according to the invention compared with the known enzyme produced under the control of nyl C.

Example III

Enzymatic Hydrolysis of PA 66 Oligomers with the Aid of a Mixture of PAM I Enzymes According to the Invention and Amidases $E_2$ Expressed by the nyl-B Gene Instead of the enzymes, the present Example utilizes their biological precursors, namely:

the recombinant strain of Example I expressing PAM I and the recombinant strain containing the nyl-B gene of Flavobacterium sp KI 72 and expressing $E_2$.

III.1 Culture of the Strains:

The strain expressing PAM I was cultivated as indicated in Example I.

The strain expressing $E_2$ is obtained by the procedure described for obtaining the strain expressing $E_3$, but by introducing plasmid pHK4 described in the reference "NEGORO et al.—Journal of Biol. Chem. (1984) 259: 13648–13651". This strain was cultured at 37° C. in M9 medium supplemented with 100 mg/l of ampicillin and inoculated at 1% (v/v) with a preculture. The preculture is composed of 10 ml of the same M9 medium supplemented with 100 mg/l of ampicillin and inoculated with colonies originating from an agar dish. When culture is complete, the cell production is determined via a dry extract obtained by the drying, overnight at 105° C., of a cell residue obtained after centrifugation (10 min at 12,000 g).

III.2 Activity of the Strains:

The cell residues, obtained as indicated above, are taken up with a 0.1 M Tris-HCl, 5 mM EDTA buffer, pH 8.0, containing 1% (v/v) of toluene, and incubated for 1 hour at 0° C. After centrifugation, the treated residues are resuspended in a 0.1 M phosphate buffer, pH 7.

The amidase activity of the cell suspensions of the strains expressing $E_2$ and PAM I was tested on the oligomers ABAB, BAB, ABA and AB.

The results are listed in Table II below.

The activity is expressed in mmol of hydrolyzed substrate/hour/g of dry cells. Operating conditions: [strain expressing PAM I]=0.125 g/l of dry extract; [oligoiners]=2.5 g/l; 0.1 M phosphate buffer, pH=7; volume 400 µl; T=30° C.; magnetic stirring.

TABLE II

| Test | Starting oligomers and hydrolysis products | Activity |
|---|---|---|
| 1 | AB → A + B | 0.11 |
| 2 | ABA → AB + A | 0.04 |
| 3 | BAB → AB + B | 131 |
| 5 | ABAB → 2 AB | 117 |

What is claimed is:

1. An isolated enzyme with amidase activity towards substrates of the amide type having at least one of the following formulae:

(I)

in which:

A and B are monomer units, $R^1$ and $R^3$ are identical or different divalent radicals representing a substituted or unsubstituted, linear or branched alkylene, an arylene or an arylalkylene, and the number of carbons in the alkylene being greater than or equal to 4,

$R^2$ corresponds to identical or different radicals selected from hydrogen and alkyl radicals having from 1 to 6 carbons, X is:
either $X^1$=OH, OM or $OR^4$, where M is selected from metals, and $R^4$ is a linear or branched alkyl containing from 1 to 6 carbon atoms,
or $X^2$= where $R^2$ and $R^3$ are as defined above and $R^5$ and $R^6$, which are identical or different, have the same definition as that given above for $R^2$, Y is:
either $Y^1$=hydrogen,
or $Y^1$= where $R^1$ is as defined above and Z is hydrogen, a radical selected from metals or a radical which is a linear or branched alkyl containing from 1 to 6 carbon atoms, with the following conditions:
if X=$X^1$, then Y=$Y^1$,
if X=$X^2$, then Y=$Y^2$ or $Y^1$,
and p is between 1.5 and 10;
or (II)

in which:

$R^2$ and $R^3$ are as defined above,

U and V respectively have the same definitions as those given above for $X^1$ and $Y^1$ in formula (I), and q=1 to 8, said enzyme being characterized by a ratio
Ra=(enzymatic activity towards amide substrates of formula (I)(E.A.(I)))/(enzymatic activity towards amide substrates of formula (II)(E.A.(II))) which is greater than 2.

2. The isolated enzyme of claim 1, wherein Z is a metal selected from the group consisting of alkali metals and alkaline earth metals.

3. An isolated enzyme according to claim 1, comprising: the peptide sequence given by the attached sequence SEQ ID NO:2, or a polypeptide having a degree of amino acid sequence homology of at least 50% with this sequence.

4. An isolated enzyme according to claim 1 which is:
active towards a substrate (I) formed by a tetramer of the type ABAB,
and capable of converting this substrate to two dimers AB with a specific enzymatic activity ($U_s$) greater than 60, which is expressed in $\mu$mol AB produced x $h^{-1}$ x $mg^{-1}$ of protein and measured at a temperature of the order of 30° C. at a pH of 7 in a phosphate buffer (100 mM), with magnetic stirring, in a volume of reaction medium of 400 $\mu$l and at a substrate concentration of 2.5 g/l.

5. An isolated enzyme according to claim 1, which is:
active towards a substrate (I) formed by a trimer BAB,
and capable of converting this trimer to a dimer AB and a monomer B with a specific enzymatic activity ($U_s$) greater than 100, which is expressed in $\mu$mol of AB produced/h.mg of enzyme and measured at a temperature of the order of 30° C., at a pH of 7 in a phosphate buffer (100 mM), with magnetic stirring, in a volume of reaction medium of 400 $\mu$l and at a substrate concentration of 2.5 g/l.

6. An isolated enzyme according to claim 1, which is:
active towards substrates (I) formed by oligomers whose degree of polymerization ($DP_n$) is between 3 and 20,
and capable of converting these oligomers to monomers B, dimers AB and trimers ABA.

7. An isolated microorganism capable of producing at least one enzyme according to claim 1.

8. A process for the hydrolysis of substrates which comprise the substrates (I) or (II), or (I) and (II) as defined in claim 1 comprising using at least one enzyme according to claim 1.

9. A process for the hydrolysis of substrates comprised of oligomers whose $DP_n$ is less than 40 and which are derived from polyamides originating from polycondensation between diacid monomers (A) and diamine monomers (B), and eventually from polyamides which are not derived from polycondensation between diacid monomers (A) and diamine monomers (B), comprising:
producing oligomers with a degree of polymerization ($DP_n$) less than or equal to 8,
and using:
at least one enzyme according to claim 1,
and at least one other type of enzyme or at least one of said enzyme's biological precursor.

10. A process according to claim 8 comprising thermal and/or chemical lysis for obtaining substrates whose $DP_n$ is such that they are hydrolyzable by the enzymatic method.

11. The process of claim 9, wherein said at least one other type of enzyme is $E_2$ produced under the control of the nyl-B gene of Flavobacterium sp KI72.

12. The process of claim 9, wherein said biological precursor is a wild-type biological precursor.

13. The process of claim 9, wherein said biological precursor is a synthetic biological precursor.

14. A process for the hydrolysis of substrates consisting at least partly of oligomers whose $DP_n$ is less than 40 and which are derived from polyamides originating from polycondensation between diacid monomers (A) and diamine monomers (B), and eventually from polyamides which are not derived from polycondensation between diacid monomers (A) and diamine monomers (B), comprising:
producing oligomers with a degree of polymerization ($DP_n$) less than or equal to 8,
and using:
at least one enzyme according to claim 1;
and at least one other type of enzyme and at least one of said enzymes biological precursor.

15. The process of claim 14, wherein said at least one other type of enzyme is $E_2$ produced under the control of the nyl-B gene of Flavobacterium sp KI72.

16. The process of claim 14, wherein said biological precursor is a wild-type biological precursor.

17. The process of claim 14, wherein said biological precursor is a synthetic biological precursor.

* * * * *

SEQUENCE LISTING

<160> NUMBER OF SEQ ID NOS: 2

<210> SEQ ID NO 1
<211> LENGTH: 1068
<212> TYPE: DNA
<213> ORGANISM: Escherichia coli
<220> FEATURE:
<221> NAME/KEY: CDS
<222> LOCATION: (1)..(1065)

<400> SEQUENCE: 1

```
atg aat acg aca ccg gtc cac gca ctc acc gac atc gac ggc ggg atc        48
Met Asn Thr Thr Pro Val His Ala Leu Thr Asp Ile Asp Gly Gly Ile
 1               5                  10                  15 gcc gtc gat ccc gca ccc cgg ctg gcc ggc cct ccg gtc ttc ggg ggt        96
Ala Val Asp Pro Ala Pro Arg Leu Ala Gly Pro Pro Val Phe Gly Gly
             20                  25                  30 ccg ggc aac gac gcc ttc gat ctc gcg ccg gtc agg agc acg ggc cgc       144
Pro Gly Asn Asp Ala Phe Asp Leu Ala Pro Val Arg Ser Thr Gly Arg
         35                  40                  45 gag atg ctg cgg ttc gac ttc ccc ggg gtc agc atc ggc gcg gcg cac       192
Glu Met Leu Arg Phe Asp Phe Pro Gly Val Ser Ile Gly Ala Ala His
     50                  55                  60 tac gag gag ggg ccc acc ggt gcg acc gtg atc cac atc ccc gcc ggc       240
Tyr Glu Glu Gly Pro Thr Gly Ala Thr Val Ile His Ile Pro Ala Gly
 65                  70                  75                  80 gcc cgc acc gcg gtg gac gcg cgg ggc ggg gcg gtg ggg ctc tcc ggc       288
Ala Arg Thr Ala Val Asp Ala Arg Gly Gly Ala Val Gly Leu Ser Gly
                 85                  90                  95 ggc tac gac ttc aac cac gcc atc tgc ctg gcc ggc gga gcc tgc tac       336
Gly Tyr Asp Phe Asn His Ala Ile Cys Leu Ala Gly Gly Ala Cys Tyr
            100                 105                 110 ggg ctc gag gcg ggc gcc ggg gtg agc gac gcg ctc ctg gaa cgc ctc       384
Gly Leu Glu Ala Gly Ala Gly Val Ser Asp Ala Leu Leu Glu Arg Leu
        115                 120                 125 gag cat cgc acc ggc ttc gcc gag ctc cag ctg gtg tcg tcg gcg gtc       432
Glu His Arg Thr Gly Phe Ala Glu Leu Gln Leu Val Ser Ser Ala Val
    130                 135                 140 atc tac gac ttc tcg gcg cgc tcc acc cgc gtc tac ccc gac aag gcg       480
Ile Tyr Asp Phe Ser Ala Arg Ser Thr Arg Val Tyr Pro Asp Lys Ala
145                 150                 155                 160 ctc ggc cgc gcg gcg ctc gaa ttc gcc gtt ccc ggt gag ttc ccg cag       528
Leu Gly Arg Ala Ala Leu Glu Phe Ala Val Pro Gly Glu Phe Pro Gln
                165                 170                 175 ggg cgg gcg ggc gcg ggc atg agc gcg tcc gcg ggc aag gtg gac tgg       576
Gly Arg Ala Gly Ala Gly Met Ser Ala Ser Ala Gly Lys Val Asp Trp
            180                 185                 190 gac cgc acc gag atc acc ggg cag ggc gcg gcg ttc cgt cgt ctc ggc       624
Asp Arg Thr Glu Ile Thr Gly Gln Gly Ala Ala Phe Arg Arg Leu Gly
        195                 200                 205 gac gtg cgc atc ctc gcc gtc gtc gtg ccg aac ccg gtc ggt gtg atc       672
Asp Val Arg Ile Leu Ala Val Val Val Pro Asn Pro Val Gly Val Ile
    210                 215                 220 gtg gac cgc gcg ggc acg gtg gtg cgc ggc aac tac gac gcg cag acc       720
Val Asp Arg Ala Gly Thr Val Val Arg Gly Asn Tyr Asp Ala Gln Thr
225                 230                 235                 240 ggg gtc cgg cgc cac ccg gtg ttc gac tac cag gag gcg ttc gcc gag       768
Gly Val Arg Arg His Pro Val Phe Asp Tyr Gln Glu Ala Phe Ala Glu
                245                 250                 255
```

```
cag gtc ccg ccc gtc acc gag gcc ggc aac acc acg atc agc gcg atc      816
Gln Val Pro Pro Val Thr Glu Ala Gly Asn Thr Thr Ile Ser Ala Ile
        260                 265                 270 gtc acg aac gtg cgg atg agc ccc gtc gag ctg aac cag ttc gcc aag      864
Val Thr Asn Val Arg Met Ser Pro Val Glu Leu Asn Gln Phe Ala Lys
        275                 280                 285 cag gtg cac agt tcg atg cac cgc ggc atc cag ccg ttc cac acc gac      912
Gln Val His Ser Ser Met His Arg Gly Ile Gln Pro Phe His Thr Asp
        290                 295                 300 atg gac ggc gac acg ctc ttc gcc gtc acc acc gac gag atc gat ctg      960
Met Asp Gly Asp Thr Leu Phe Ala Val Thr Thr Asp Glu Ile Asp Leu
305                 310                 315                 320 ccg acg acc ccg ggg tcg tcg cgc ggg cgg ctg tcg gtg aac gcg acc     1008
Pro Thr Thr Pro Gly Ser Ser Arg Gly Arg Leu Ser Val Asn Ala Thr
        325                 330                 335 gcg ctc ggc gcg atc gcc tcc gag gtg atg tgg gac gcc gtc ctc gag     1056
Ala Leu Gly Ala Ile Ala Ser Glu Val Met Trp Asp Ala Val Leu Glu
        340                 345                 350 gcc ggc aag tag                                                     1068
Ala Gly Lys
        355
```

<210> SEQ ID NO 2
<211> LENGTH: 355
<212> TYPE: PRT
<213> ORGANISM: Escherichia coli

<400> SEQUENCE: 2

```
Met Asn Thr Thr Pro Val His Ala Leu Thr Asp Ile Asp Gly Gly Ile
 1               5                   10                  15

Ala Val Asp Pro Ala Pro Arg Leu Ala Gly Pro Val Phe Gly Gly
                20                  25                  30

Pro Gly Asn Asp Ala Phe Asp Leu Ala Pro Val Arg Ser Thr Gly Arg
            35                  40                  45

Glu Met Leu Arg Phe Asp Phe Pro Gly Val Ser Ile Gly Ala Ala His
    50                  55                  60

Tyr Glu Glu Gly Pro Thr Gly Ala Thr Val Ile His Ile Pro Ala Gly
65                  70                  75                  80

Ala Arg Thr Ala Val Asp Ala Arg Gly Gly Ala Val Gly Leu Ser Gly
                85                  90                  95

Gly Tyr Asp Phe Asn His Ala Ile Cys Leu Ala Gly Gly Ala Cys Tyr
            100                 105                 110

Gly Leu Glu Ala Gly Ala Gly Val Ser Asp Ala Leu Leu Glu Arg Leu
        115                 120                 125

Glu His Arg Thr Gly Phe Ala Glu Leu Gln Leu Val Ser Ser Ala Val
    130                 135                 140

Ile Tyr Asp Phe Ser Ala Arg Ser Thr Arg Val Tyr Pro Asp Lys Ala
145                 150                 155                 160

Leu Gly Arg Ala Ala Leu Glu Phe Ala Val Pro Gly Glu Phe Pro Gln
                165                 170                 175

Gly Arg Ala Gly Ala Gly Met Ser Ala Ser Ala Gly Lys Val Asp Trp
            180                 185                 190

Asp Arg Thr Glu Ile Thr Gly Gln Gly Ala Ala Phe Arg Arg Leu Gly
        195                 200                 205

Asp Val Arg Ile Leu Ala Val Val Pro Asn Pro Val Gly Val Ile
    210                 215                 220

Val Asp Arg Ala Gly Thr Val Val Arg Gly Asn Tyr Asp Ala Gln Thr
```

-continued

```
225                 230                 235                 240
Gly Val Arg Arg His Pro Val Phe Asp Tyr Gln Glu Ala Phe Ala Glu
                245                 250                 255

Gln Val Pro Pro Val Thr Glu Ala Gly Asn Thr Thr Ile Ser Ala Ile
                260                 265                 270

Val Thr Asn Val Arg Met Ser Pro Val Glu Leu Asn Gln Phe Ala Lys
            275                 280                 285

Gln Val His Ser Ser Met His Arg Gly Ile Gln Pro Phe His Thr Asp
        290                 295                 300

Met Asp Gly Asp Thr Leu Phe Ala Val Thr Thr Asp Glu Ile Asp Leu
305                 310                 315                 320

Pro Thr Thr Pro Gly Ser Ser Arg Gly Arg Leu Ser Val Asn Ala Thr
                325                 330                 335

Ala Leu Gly Ala Ile Ala Ser Glu Val Met Trp Asp Ala Val Leu Glu
                340                 345                 350

Ala Gly Lys
        355
```